United States Patent
Koehler

(10) Patent No.: US 8,698,103 B2
(45) Date of Patent: Apr. 15, 2014

(54) MEASURING DEVICE FOR DETERMINATION OF AT LEAST ONE PARAMETER OF A BLOOD SAMPLE

(75) Inventor: Hans Koehler, Graz (AT)

(73) Assignee: Smart Medical Solutions GmbH, Graz (AT)

(*) Notice: Subject to any disclaimer, the term of this patent is extended or adjusted under 35 U.S.C. 154(b) by 388 days.

(21) Appl. No.: 13/144,979

(22) PCT Filed: Jan. 12, 2010

(86) PCT No.: PCT/EP2010/050239
§ 371 (c)(1),
(2), (4) Date: Aug. 30, 2011

(87) PCT Pub. No.: WO2010/081790
PCT Pub. Date: Jul. 22, 2010

(65) Prior Publication Data
US 2012/0037816 A1     Feb. 16, 2012

(30) Foreign Application Priority Data
Jan. 19, 2009 (AT) .................................. A 79/2009

(51) Int. Cl.
*G01N 21/64* (2006.01)
*H01J 37/20* (2006.01)

(52) U.S. Cl.
USPC ..................................... 250/461.2; 250/458.1

(58) Field of Classification Search
USPC .............. 250/458.1, 461.2; 422/82.05, 82.06, 422/82.07, 82.08, 82.09
See application file for complete search history.

(56) References Cited

U.S. PATENT DOCUMENTS

| 4,968,632 A | * | 11/1990 | Brauer et al. ................. 436/136 |
| 5,779,978 A | | 7/1998 | Hartmann |
| 6,652,810 B1 | | 11/2003 | Ziegler |
| 2003/0190262 A1 | | 10/2003 | Blazewicz |

FOREIGN PATENT DOCUMENTS

| EP | 0175352 A2 | 3/1986 |
| EP | 0175352 B1 | 6/1991 |
| EP | 0793090 A1 | 9/1997 |
| EP | 1130382 B1 | 5/2001 |
| EP | 1106987 A2 | 6/2001 |
| WO | 2002059585 A2 | 8/2002 |

OTHER PUBLICATIONS

International Search Report for International Application No. PCT/EP2010/050239 mailed May 10, 2010.

* cited by examiner

*Primary Examiner* — David Porta
*Assistant Examiner* — Kenneth J Malkowski
(74) *Attorney, Agent, or Firm* — RatnerPrestia

(57) ABSTRACT

Measuring devices are disclosed for determination of at least one parameter of a blood sample. The measuring device includes a flow-through measuring cell, in which is disposed luminescence-optical sensor elements, which can be brought into contact with the blood sample, and at least one light source for excitation of the luminescence-optical sensor element and at least one photodetector for receiving the luminescence radiation emitted by the luminescence-optical sensor element. The light source and the photodetector are located on opposite sides of the flow-through measuring cell. The sensor elements are placed on an excitation side of the flow-through measuring cell, which faces the light source, and the light source emits excitation radiation of wavelength less than 600 nm, while the luminescence radiation of the sensor elements lies in a wavelength range greater than 600 nm, thus exposing the excitation radiation to stronger absorption by the blood sample than the luminescence radiation.

10 Claims, 2 Drawing Sheets

MEASURING DEVICE FOR DETERMINATION OF AT LEAST ONE PARAMETER OF A BLOOD SAMPLE

CROSS REFERENCE TO RELATED APPLICATIONS

This application is the U.S. national phase application of PCT International Application No. PCT/EP2010/050239, filed Jan. 12, 2010, which claims priority to Austrian Patent Application No. A79/2009, filed Jan. 19, 2009, the contents of these applications being incorporated fully by reference herein.

FIELD OF THE INVENTION

The invention relates to a measuring device for determining at least one parameter of a blood sample, comprising a flow-through measuring cell, in which is disposed at least one luminescence-optical sensor element, which can be brought into contact with the blood sample, and at least one light source for exciting the luminescence-optical sensor element, and at least one photodetector for receiving the luminescence radiation emitted by the luminescence-optical sensor element, the light source and the photodetector being located on opposite sides of the flow-through measuring cell.

BACKGROUND OF THE INVENTION

From EP 0 175 352 B1 there is known a method and apparatus for rapid determination of the parameters of a sample medium. The apparatus is provided with a flow-through measuring cell for gases and fluids, which is suitable for simultaneous determination of a plurality of parameters, a transparent, luminescent sensor layer in the flow-through cell being in contact with the sample. The variables to be measured are oxygen concentration and temperature, the measured luminescence radiation having a wavelength of 650 nm, respectively 720 nm, while the excitation radiation has a shorter wavelength. Excitation is effected by means of LEDs and radiation detection by means of photodiodes, these elements being located on opposite sides of the flow-through measuring cell. Since the luminescent sensor layer is placed on the side of the detectors, the excitation radiation on its way to the luminescent layer must pass through the sample medium. In the case of absorbent fluids, such as blood, this is a disadvantage as the excitation radiation is appreciably attenuated by the medium to be measured.

From EP 1 130 382 B1 there is further known an optical sensor for the determination of a number of analytes in a fluid sample, where a plurality of optical sensors is in contact with the fluid sample. The arrangement comprises light sources providing excitation radiation and detectors for determining the light interaction by the sensors, and has a processor which evaluates the concentration of each analyte in the fluid sample from the measured light interaction. Among other purposes the sensor is used to measure glucose in blood with concomitant determination of $O_2$ concentration and temperature.

There are also known measurement arrangements (EP 1 106 987 B1) in which both optical components (light source and detector) contact the sensor layer in the flow-through measuring cell on one and the same side, parts of the measuring cell being transparent and acting as light guides for the measuring radiation and excitation radiation.

From WO 2002/059585 A2 there is known a measurement arrangement for determination of the oxygen content of a gas, for instance breathing air. The measuring device comprises a flow-through measuring cell, in which is disposed a luminescence-optical sensor element in contact with the gas flow. Two reflection geometries are described as possible measuring geometries, where the radiation source for the excitation radiation and the detector receiving the luminescence radiation are located on the same side of the flow-through measuring cell. There is also described a transmitted-light geometry where the luminescence-optical sensor element is placed on the detector side of the flow-through measuring cell.

SUMMARY OF THE INVENTION

Aspects of the present invention achieve an improvement of signal quality in a measuring device for the determination of at least one parameter of a blood sample, where the measuring apparatus should be easy to manufacture and of low cost.

Signal quality improvement may be achieved by the invention by positioning the at least one luminescence-optical sensor element at the excitation side of the flow-through measuring cell, which faces the light source, by providing that the light source emits excitation radiation of wavelength less than 600 nm, for instance 425 nm, and by further providing that the luminescence radiation of the luminescence-optical sensor elements lies in a wavelength range greater than 600 nm, thus exposing the excitation radiation to much stronger absorption by the blood sample than the luminescence radiation.

Aspects of the invention exploit the fact that radiation absorption by blood is largely wavelength-dependent, as is for instance shown in the diagram of FIG. 5. The diagram shows absoption $\mu_a$ as a function of wavelength $\lambda$ for oxygenated (solid line) and for deoxygenated (dashed line) blood. The diagram is taken from Faber et al.: "Oxygen Saturation-Dependent Absorption and Scattering of Blood"; Physical Review Letters, 2004, and treats differences in absorption behaviour of oxygenated and deoxygenated blood. It can for instance be seen from the diagram that excitation radiation $\lambda_a$ in the wavelength region about 425 nm is far more strongly absorbed in blood than luminescence radiation $\lambda_L$ emitted by optical sensors in the wavelength region around 780 nm. In the example shown the excitation light is attenuated by a factor 100 relative to the luminescence light. By placing the luminescence-optical sensor elements on the excitation side of the flow-through measuring cell as the invention proposes, the blood sample will act as a filter on the excitation radiation and the luminescence radiation emitted by the sensor elements will be given preference in reaching the photodetectors.

According to aspects of the invention the optical sensor elements are placed in a linear array along the axis of the flow-through measuring cell on the excitation side of the flow-through measuring cell, each sensor element being assigned a light source and, on the opposite side of the flow-through measuring cell, a photodetector.

A further advantage of aspects of the invention compared to the state of the art as for instance given in EP 0 175 352 B1, lies in the fact that the flow-through measuring cell can exchangeably be inserted in a two-part measuring sleeve, whose excitation part contains the light sources, preferably LEDs, together with excitation electronics and whose measuring part contains the photodetectors, preferably photodiodes, together with the measuring electronics. The light sources and the detectors are thus located in spatially separated circuits, and electronic interference between the individual components is avoided. The blood sample is sufficiently transparent only for wavelengths greater than 600 nm, the excitation radiation has shorter wavelength, for instance 425 nm.

In an advantageous embodiment of the invention the excitation side of the flow-through measuring cell has a mirror layer in the area of the luminescence-optical sensors, which is transparent for the excitation radiation but reflects the luminescence radiation. By this mirror layer radiation components of the luminescence radiation emitted in the direction of the light source are redirected towards the photodetector and the net signal is thus strengthened.

In the case of phase measurement at least one reference light source is placed on the excitation side of the measuring cell, whose reference radiation passes through the flow-through measuring cell and enters the photodetectors located on the opposite side.

BRIEF DESCRIPTION OF THE DRAWINGS

The invention will now be described in more detail with reference to the enclosed drawings.

DETAILED DESCRIPTION OF THE INVENTION

Figure 1:
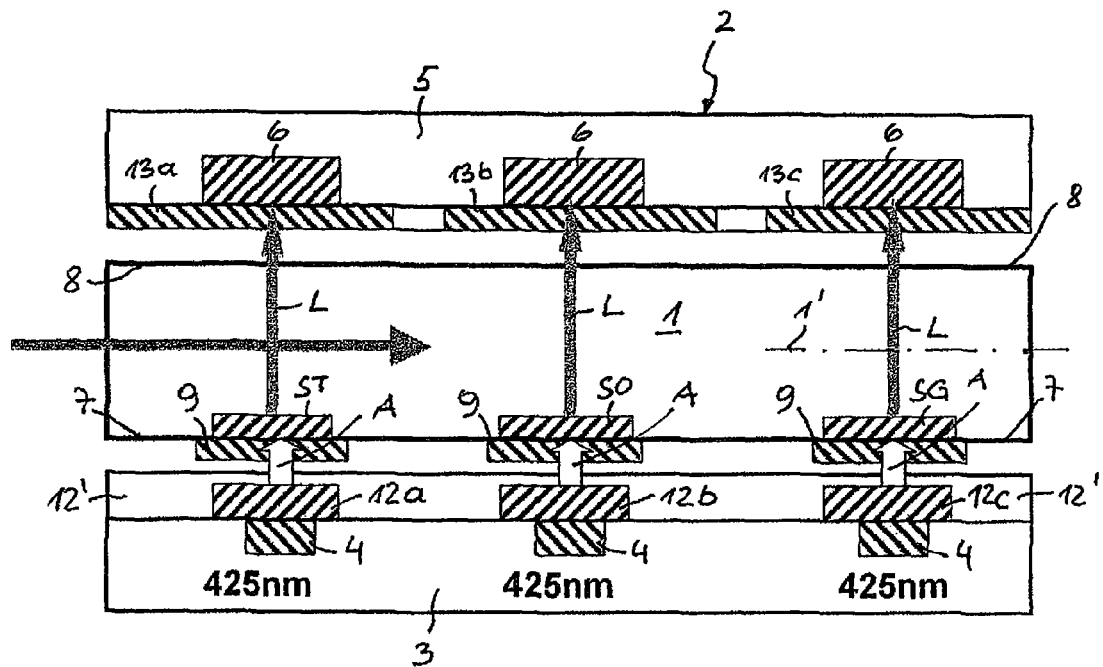
FIG. 1 is an illustration of a first variant of a measuring device for determination of at least one parameter of a blood sample in a schematic longitudinal section in accordance with one aspect of the present invention.

The measuring device for determination of at least one parameter of a blood sample shown in FIG. 1 comprises a flow-through measuring cell 1, in which are disposed for instance three luminescence-optical sensor elements ST (temperature), SO (oxygen) and SG (glucose), which are brought into contact with the blood sample during the measurement process. The flow-through measuring cell 1 is exchangeably disposed in a two-part measuring sleeve 2 (inserted, snapped in place), whose excitation part 3 contains the light sources 4 assigned to the individual sensor elements and the excitation filters 12a to 12c with the excitation electronics (not further shown here), while the measuring part 5 of the measuring sleeve 2 contains the photodetectors 6 and measuring filters 13a to 13c together with the measuring electronics (not further shown). The light sources 4 and the photodetectors 6 are located on opposing sides 7, 8 (excitation side 7 and measuring side 8) of the flow-through measuring cell 1.

Since the luminescence-optical sensor elements ST, SO and SG are located on the excitation side 7 of the flow-through measuring cell 1 facing the light source 4, the luminescence radiation L originating in the sensor element and part of the excitation radiation A will pass through the blood sample. The excitation radiation A is attenuated to a far greater degree by absorption in the blood sample than the luminescence radiation, which has longer wavelength. The sample will thus provide a filtering effect which has a positive effect on the measurement and will thus improve signal quality.

The luminescence-optical sensor elements ST, SO and SG are preferably disposed in a linear array along the measurement cell axis 1', each sensor element being assigned a light source 4 and, on the opposite measuring side 8 of the flow-through measuring cell 1, a photodetector 6.

The measuring device shown in FIG. 1 may for instance be used for decay time measurement, i.e. the measured decay time of luminescence intensity after excitation of the luminescence-optical sensor elements furnishes a measure for the quantity to be measured.

Figure 3:
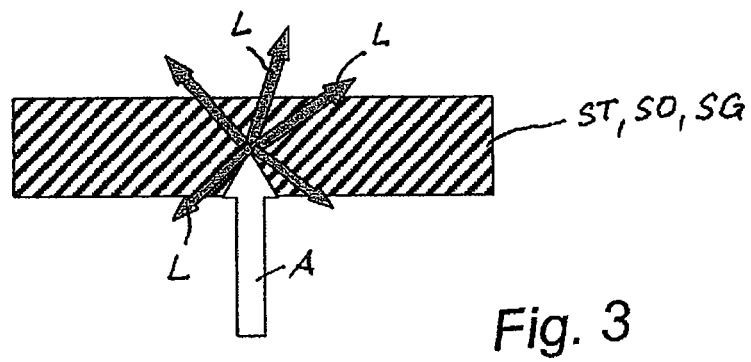
FIG. 3 and FIG. 4 are illustrations depicting details of the measuring devices of FIGS. 1 and 2.
Figure 4:
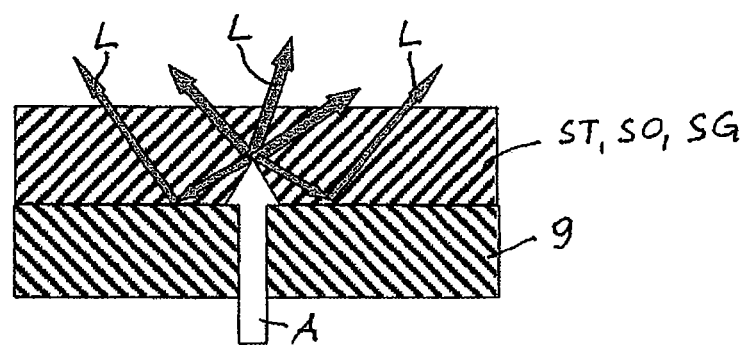
Figure 5:
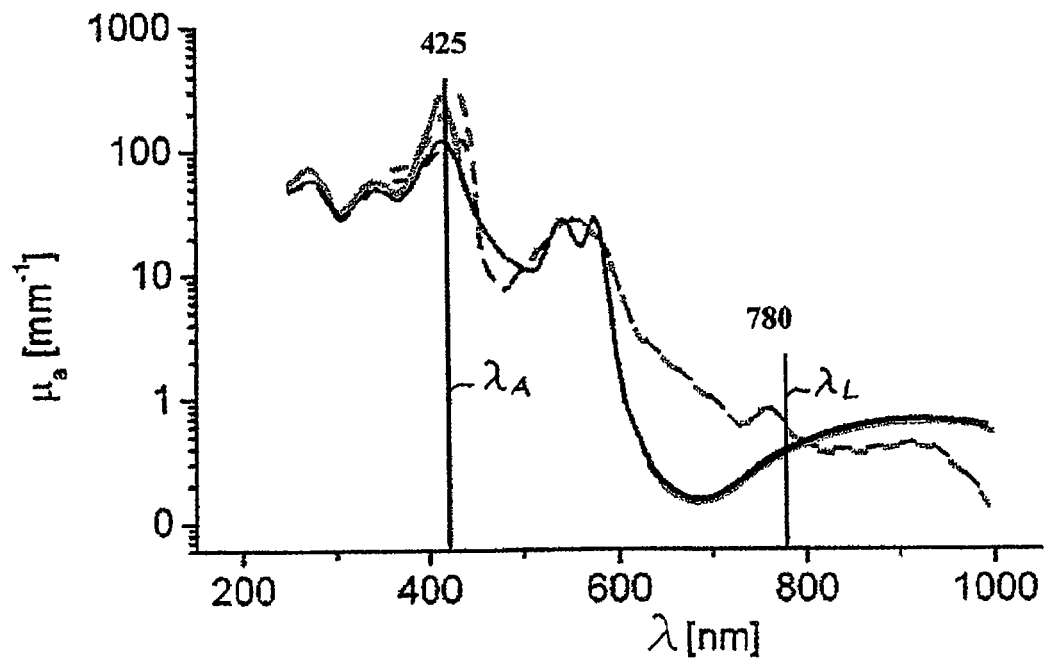
FIG. 5 is a graph of the absorption of a blood sample in a wavelength λ range of 200 nm to 1,000 nm in accordance with aspects of the present invention.

As for instance shown in FIG. 1, the excitation side 7 of the flow-through measuring cell 1 may be provided with a mirror layer 9 in the area of the luminescence-optical sensor elements ST, SO, SG. The effect of the mirror layer is presented in FIGS. 3 and 4. The excitation radiation A impinges on the luminescence-optical sensor element ST, SO or SG, generating luminescence radiation L in all spatial directions. Without the mirror layer (see FIG. 3) those portions of radiation that are emitted towards the light source will not contribute to the measurement signal.

If a mirror layer is applied (FIG. 4), which is transparent for radiation with wavelength less than 600 nm and reflects radiation with wavelength greater than 600 nm, portions of the luminescence radiation L are additionally reflected into the detector and augment the measurement signal.

Figure 2:
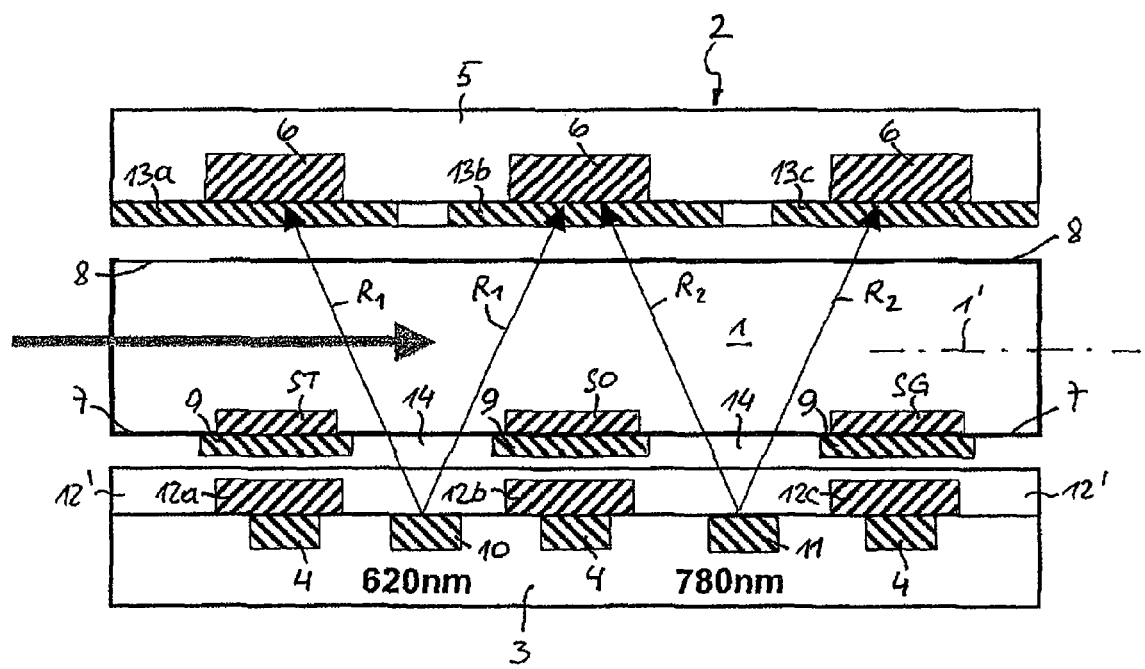
FIG. 2 is an illustration of a second variant of the measuring device in a sectional view according to FIG. 1 in accordance with one aspect of the present invention.

The measuring device shown in FIG. 2 may for instance be used for phase measurement, where a reference signal must be obtained for referencing the measurement signal. According to the invention at least one reference light source 10 and/or 11 is provided on the excitation side 7 of the flow-through measuring cell 1, whose reference radiation $R_1$, $R_2$ passes through the flow-through measuring cell 1 and is detected by photodetectors 6 placed on the opposite measuring side 8. There may for instance be provided a first reference light source 10 with reference radiation $R_1$ in the 620 nm range and a second reference light source 11 with reference radiation $R_2$ in the 780 nm range, both being preferably positioned in the excitation part 3 of the two-part measuring sleeve 2. In the mirror layer 9 on the excitation side 7 of the flow-through measuring cell 1 openings 14 are provided through which the reference radiation may enter the flow-through measuring cell 1.

In FIG. 1 as well as in FIG. 2 excitation filters 12a, 12b, 12c are provided between the light sources 4 and the luminescence-optical sensor elements ST, SO, SG; the light sources 4 could also be embedded in a common filter layer 12'. Measuring filters 13a, 13b and 13c are provided on the entry side of the photodetectors 6.

The LEDs of the light sources 4 may for instance emit excitation radiation of wavelength less than 600 nm, for instance 425 nm, while the luminescence radiation of the luminescence-optical sensor elements ST, SO, SG lies in the wavelength range greater than 600 nm, for instance close to 780 nm.

Summing up, advantages of the measuring device according to aspects of the invention include one or more of the following:

very simple optical configuration;
flat design of the flow-through measuring cell 1 and the measuring sleeve 2;
great signal intensity, because the photodetectors may be of larger size;
no electrical cross-talk (minimal signal background), because the excitation part 3 and the measuring part 5 of the measuring sleeve 2 are spatially separated;
identification of the sample (blood sample or rinsing fluid) is effected by measuring signal intensity;
simultaneous photometric characterisation of the blood sample (haemoglobin content and oxygenation);
parallel determination of arterial $pO_2$.

The invention claimed is:

1. A measuring device for determination of at least one parameter of a blood sample, comprising:
   a flow-through measuring cell, in which is disposed at least one luminescence-optical sensor element, which can be brought into contact with the blood sample;
   at least one light source for excitation of the at least one luminescence-optical sensor element; and
   at least one photodetector for receiving luminescence radiation emitted by the at least one luminescence-optical sensor element,
   wherein the at least one light source and the at least one photodetector are located on opposite sides of the flow-through measuring cell, the at least one luminescence-optical sensor element is placed on an excitation side of the flow-through measuring cell which faces the at least one light source, the at least one light source emits excitation radiation of wavelength less than 600 nm, and the luminescence radiation of the at least one luminescence-optical sensor elements lies in a wavelength range greater than 600 nm.

2. The measuring device of claim 1, wherein the at least one luminescence-optical sensor elements are provided on the excitation side of the flow-through measuring cell, in a linear array along a measuring cell axis, each sensor element assigned one of the at least one light source and, on an opposite measuring side of the flow-through measuring cell, a photodetector.

3. The measuring device of claim 1, wherein the flow-through measuring cell can exchangeably be inserted into a two-part measuring sleeve, whose excitation part contains the at least one light source and excitation electronics, and whose measuring part contains the photodetectors, and measuring electronics.

4. The measuring device of claim 1, wherein the excitation side of the flow-through measuring cell is provided with a mirror layer in an area of the luminescence-optical sensor elements, the mirror layer transparent for the excitation radiation and reflective for the luminescence radiation.

5. The measuring device of claim 1, wherein on the excitation side of the flow-through measuring cell at least one reference light source is provided, whose reference radiation passes through the flow-through measuring cell and reaches the at least one photodetector on an opposite measuring side.

6. The measuring device according to claim 5, wherein a first reference light source with reference radiation about 620 nm and a second reference light source with reference radiation about 780 nm is provided, the reference light sources located in an excitation part of a two-part measuring sleeve.

7. The measuring device of claim 1, wherein excitation filters are positioned between the at least one light source and the at least one luminescence-optical sensor elements.

8. The measuring device of claim 1, wherein measuring filters are provided on an entry side of the at least one photodetector.

9. The measuring device of claim 1, wherein the flow-through measuring cell contains at least one $O_2$-sensor, at least one glucose sensor and at least one temperature sensor.

10. The measuring device of claim 1, wherein the at least one light source is embedded in a filter layer.

* * * * *

UNITED STATES PATENT AND TRADEMARK OFFICE
CERTIFICATE OF CORRECTION

PATENT NO. : 8,698,103 B2  Page 1 of 1
APPLICATION NO. : 13/144979
DATED : April 15, 2014
INVENTOR(S) : Hans Koehler It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 429 days.

Signed and Sealed this

Twenty-ninth Day of September, 2015

Michelle K. Lee
*Director of the United States Patent and Trademark Office*